United States Patent [19]
Cooper et al.

[11] Patent Number: 5,705,181
[45] Date of Patent: Jan. 6, 1998

[54] METHOD OF MAKING ABSORBABLE POLYMER BLENDS OF POLYLACTIDES, POLYCAPROLACTONE AND POLYDIOXANONE

[75] Inventors: Kevin Cooper, Warren; Steven C. Arnold, Sparta; Angelo Scopelianos, Whitehouse Station, all of N.J.

[73] Assignee: Ethicon, Inc., Somerville, N.J.

[21] Appl. No.: 688,585

[22] Filed: Jul. 30, 1996

Related U.S. Application Data

[62] Division of Ser. No. 320,634, Oct. 11, 1994, Pat. No. 5,641,501.
[51] Int. Cl.⁶ .......................... A61K 47/34; B28B 1/100
[52] U.S. Cl. .......................... 424/426; 425/2
[58] Field of Search ................ 424/426; 525/411, 525/413, 415, 471; 425/2; 264/176.1, 175, 500

[56] References Cited

U.S. PATENT DOCUMENTS

| 5,047,048 | 9/1991 | Be Zwada et al. |
| 5,320,624 | 6/1994 | Kaplan et al. |

*Primary Examiner*—Edward J. Webman
*Attorney, Agent, or Firm*—Emil Richard Skula

[57] ABSTRACT

Absorbable binary and tertiary blends of homopolymers and copolymers of poly(lactide), poly(glycolide), poly($\epsilon$-caprolactone), and poly(p-dioxanone) are described. The blends when used to manufacture medical devices exhibit shape retention, dimensional stability and palpability without loss of the strength, stiffness and BSR found for poly(lactide) homopolymers and/or poly(lactide-co-glycolide) copolymers.

2 Claims, 3 Drawing Sheets

METHOD OF MAKING ABSORBABLE POLYMER BLENDS OF POLYLACTIDES, POLYCAPROLACTONE AND POLYDIOXANONE

This is a division, of application Ser. No. 08/320,634, filed Oct. 11, 1994, now U.S. Pat. No. 5,641,501 (issued Feb. 24, 1997) which is hereby incorporated by reference.

TECHNICAL FIELD

The field of art to which this invention relates is polymers, more specifically, biocompatible, absorbable binary and tertiary polymer blends. Especially, blends of poly(lactide-co-glycolide) with poly(ε-caprolactone) and poly(p-dioxanone) polymers.

BACKGROUND OF THE INVENTION

Polymers, including homopolymers and copolymers, which are both biocompatible and absorbable in vivo are well known in the art. Such polymers are typically used to manufacture medical devices which are implanted in body tissue and absorb over time. Examples of such medical devices manufactured from these absorbable biocompatible polymers include suture anchors, sutures, staples, surgical tacks, clips, plates and screws, etc.

Absorbable, biocompatible polymers useful for manufacturing medical devices include both natural and synthetic polymers. Natural polymers include cat gut, cellulose derivatives, collagen, etc. Synthetic polymers include aliphatic polyesters, polyanhydrides, poly(ortho)esters, and the like. Natural polymers typically absorb by an enzymatic degradation process in the body, while synthetic absorbable polymers typically degrade by a hydrolytic mechanism.

Synthetic absorbable polymers which are typically used to manufacture medical devices include homopolymers such as poly (glycolide), poly(lactide), poly (ε-caprolactone), poly (trimethylene carbonate) and poly(p-dioxanone) and copolymers such as poly(lactide-co-glycolide), poly(ε-caprolactone-co-glycolide), and poly(glycolide-co-trimethylene carbonate). The polymers may be statistically random copolymers, segmented copolymers, block copolymers, or graft copolymers. It is also known that both homopolymers and copolymers can be used to prepare blends.

There is a constant need in this art for new polymer compositions having improved physical properties when molded or extruded into medical devices and further having excellent in vivo properties. For example, it is known that poly(lactide) and many copolymers of lactide and glycolide rich in lactide repeating units have superior in vivo properties. However, molded articles manufactured from these copolymers are known to have poor dimensional stability due to a lack of crystallinity.

Additionally, for certain applications, such as plate and screw fixation devices, it is necessary to be able to bend the device and then retain the shape of the device to the contours of a body structure.

Furthermore, such devices should have excellent palpability. That is, the device, in vivo, should be able to soften and dissolve away slowly upon absorption, rather than fragmenting into small granules which can cause tissue reaction.

Accordingly, what is needed in this art are novel polymer mixtures which have improved dimensional stability, shape retention, and palpability, while retaining the excellent strength, stiffness and breaking strength retention (BSR) found in poly(lactide) homopolymers and poly(lactide-co-glycolide) copolymers. Breaking strength retention is a conventionally known standard method of measuring the strength of a device made of a bioabsorbable polymer as a function of time under biological conditions in vitro or as a function of time after being implanted in vivo.

As described in U.S. Pat. Nos. 5,080,665 and 5,320,624 and Canadian applications 2,079,274 and 2,079,275, various ductile, bioabsorbable polymers (e.g., poly(ε-caprolactone), poly(trimethylene carbonate), and poly(p-dioxanone)) have been blended with amorphous or low crystallinity poly (lactide) hompolymers and poly(lactide-co-glycolide) copolymers to improve device bendability at room temperature and their resistance to stress cracking. By the addition of these ductile polymers to the blend, the stiffness of the material decreases to a point where it is possible to bend the device. Upon bending, crazes form, creating voids in the device which lead to permanent deformation. However, because of void formation, local stress concentrations may form, which can often lead to an unsatisfactory decrease in stiffness, strength and BSR.

Therefore, to this end, it would be highly desirable to develop blends which were not dependent upon large additions of a ductile polymer to create bendability in the fixation device, but were dependent upon smaller additions of a low melting polymer, in which the molded or extruded device when heated above the melting point of this low melting polymer could be bent or shaped to the contours of the fracture that is to be fixated. Once shaped, the device could be cooled to room or body temperature, recrystallizing the low melting polymer of the blend, and thereby, locking the newly formed shape of the device in place.

Additionally, since only small amounts of this low melting polymer or copolymer would be incorporated into the blend, the excellent strength, stiffness and BSR of the major phase of the blend, poly(lactide) hompolymer or poly (lactide-co-glycolide) copolymer, would be retained.

DISCLOSURE OF THE INVENTION

Accordingly, a novel, absorbable, biocompatible, polymer blend is disclosed. The polymer blend comprises a minor phase of about 0.1 weight percent to about 9.9 weight percent of a mixture of homopolymers of poly(ε-caprolactone) and poly(p-dioxanone), or a blocky, segmented, statistically random, or branched copolymer of ε-caprolactone and p-dioxanone, with the remaining portion of the blend comprising a major phase of poly(lactide) homopolymer and/or poly(lactide-co-glycolide) copolymer.

Yet another aspect of the present invention is a biomedical device, especially implantable wound closure devices such as suture anchors, surgical staples, clips, sutures, plates and screws, comprising the above-described polymer blends.

Another aspect of the present invention is a medical device manufactured from the above-described polymer blends of the present invention which can be heated above the melting point of the minor phase of the blend, then shaped to conform to a body structure, and then cooled to body temperature to retain the newly formed shape when implanted in vivo.

Still yet another aspect of the present invention is a method of conforming a medical device to a body structure. The method entails using a medical device manufactured from the above-described polymer blends. Then, heating the device above the melting point of the minor phase of the blend, and shaping the device to conform to the shape of the body structure.

The foregoing and other features and advantages of the invention will become more apparent from the following description and accompanying examples.

DESCRIPTION OF THE PREFERRED EMBODIMENTS

Figure 1:
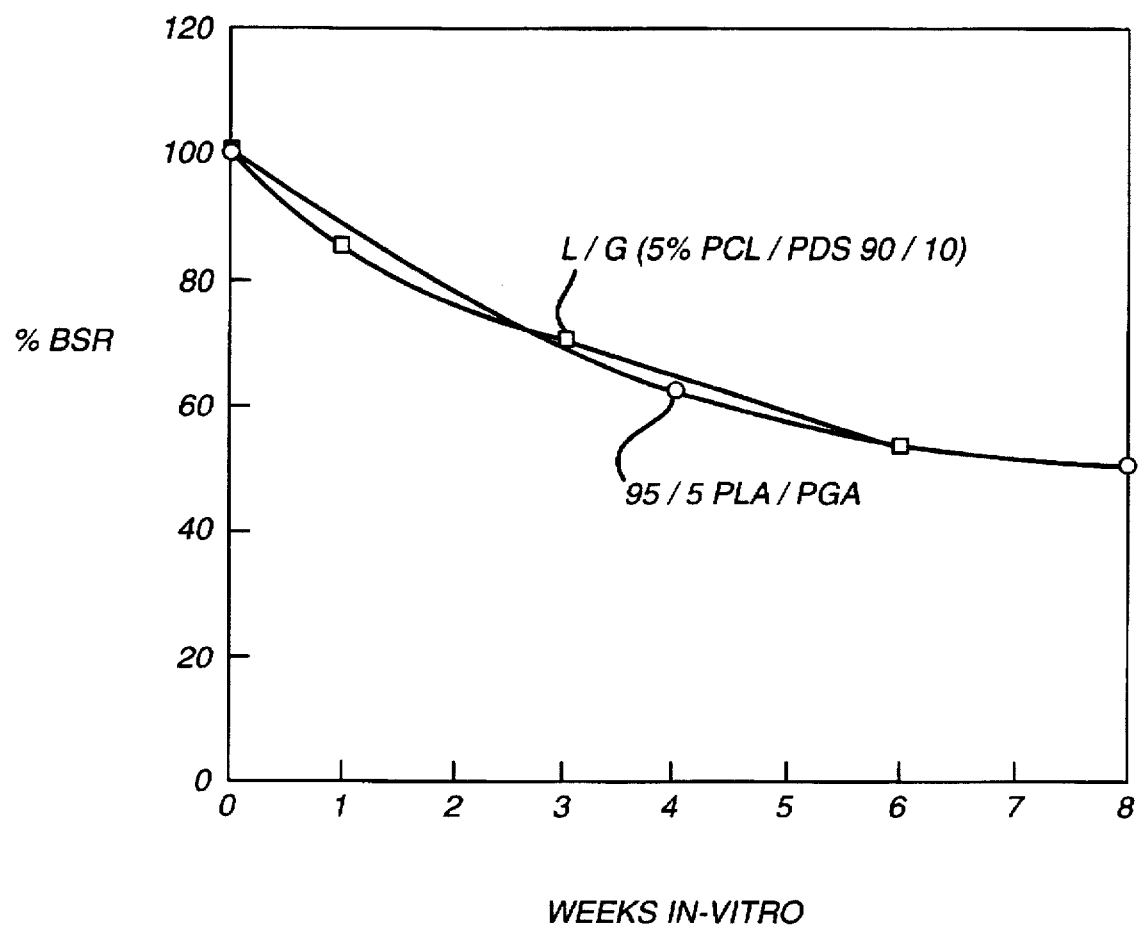
FIG. 1 is a graph illustrating the in vitro BSR profiles of a blend composed of 95 weight percent of a 95:5 (mol/mol) poly(lactide-co-glycolide) copolymer and 5 weight percent of a 90:10 (mol/mol) poly(ε-caprolactone-co-p-dioxanone) copolymer, and a 95:5 (mol/mol) poly(lactide-co-glycolide) copolymer.

The aliphatic polyesters useful in the practice of the present invention will typically be synthesized by conventional techniques using conventional processes. For example, in a ring opening polymerization, the aliphatic lactone monomers are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol, a glycol, a hydroxyacid, or an amine, and is present in the monomer mixture at a molar ratio of monomer to initiator ranging from about 100/1 to about 5000/1. The polymerization is typically carried out at a temperature range from about 80° C. to about 220° C., preferably from about 160° C. to about 200° C., until the desired molecular weight and viscosity are achieved.

Under the above described conditions, the homopolymers and copolymers will typically have a weight average molecular weight of about 10,000 grams per mole to about 200,000 grams per mole, more typically about 20,000 grams per mole to about 100,000 grams per mole, and most preferably about 40,000 grams per mole to about 70,000 grams per mole. Polymers of these molecular weight exhibit inherent viscosities between about 0.1 to about 3.0 deciliters per gram (dL/g), more typically about 0.2 to about 2.5 dL/g, and most preferably about 0.4 to about 2.0 dL/g as measured in a 0.1 g/dL solution of hexafluoroisopropanol (HFIP) at 25° C.

Suitable aliphatic lactone monomers may be selected from the group consisting of glycolide, lactide (l, d, dl, meso), p-dioxanone, trimethylene carbonate, ε-caprolactone, delta-valerolactone, beta-butyrolactone, epsilon-decalactone, 2,5-diketomorpholine, pivalolactone, alpha, alphadiethylpropiolactone, ethylene carbonate, ethylene oxalate, 3-methyl-1,4-dioxane-2,5-dione, 3,3-diethyl-1, 4-dioxan-2,5-dione, gamma-butyrolactone, 1,4-dioxepan-2-one, 1,5-dioxepan-2-one, 1,4-dioxan-2-one, 6,8-dioxabicyclooctane-7-one and combinations of two or more thereof. Preferred lactone monomers are selected from the group consisting of glycolide, lactide, p-dioxanone, and ε-caprolactone.

Most preferably, the aliphatic polyesters consist of poly (ε-caprolactone), poly(p-dioxanone), and poly(lactide) homopolymers, and poly(ε-caprolactone-co-p-dioxanone) and poly(lactide-co-glycolide) copolymers.

The poly(lactide-co-glycolde) copolymers will contain sufficient amounts of glycolide repeating units to effectively provide faster bioabsorption while still providing a reasonably long BSR profile. The poly(lactide-co-glycolide) copolymers will typically contain about 25 mole percent to about 99 mole percent of lactide repeating units, and more preferably about 50 mole percent to about 95 mole percent of lactide repeating units. The lower limit of lactide repeating units in the copolymer is desirable because the presence of 50 mole percent of glycolide repeating units provides faster bioabsorption to the copolymer. The upper limit of lactide repeating units in the copolymer is desirable because it provides a long BSR profile to the copolymer.

The poly(ε-caprolactone-co-p-dioxanone) copolymers will contain sufficient amounts of ε-caprolactone repeating units to effectively provide acceptable bioabsorption and BSR profiles. The poly(ε-caprolactone-co-p-dioxanone) copolymers will preferably consist of about 5 mole percent to about 95 mole percent of ε-caprolactone repeating units. Most preferably, the poly(ε-caprolactone-co-p-dioxanone) copolymers will consist of about 50 mole percent to about 95 mole percent of ε-caprolactone repeating units. The lower and upper limits of ε-caprolactone repeating units provide for copolymers with a desirable range of BSR profiles, absorptions, and crystallinity for bendability characteristics.

The polymer blends of the present invention are manufactured in a conventional manner, preferably in the following manner. The homopolymers and copolymers are individually charged into a conventional mixing vessel having a conventional mixing device mounted therein such as an impeller or equivalents thereof. Then, the polymers and copolymers are mixed at a temperature of about 150° C. to about 220° C., more preferably from about 160° C. to about 200° C., for about 5 to about 90 minutes, more preferably for about 10 to about 45 minutes, until a uniformly dispersed polymer blend is obtained. Then, the polymer blend is further processed by removing it from the mixing device, cooling to room temperature, grinding, and drying under pressures below atmospheric at elevated temperatures for a period of time using conventional apparatuses and processes.

The binary polymer blends of the present invention will have sufficient amounts of poly(ε-caprolactone-co-p-dioxanone) copolymers to effectively impart sufficient shapeability and palpability to the blend while retaining the strength, stiffness, and BSR properties of the poly(lactide) homopolymer and/or poly(lactide-co-glycolide) copolymers. The blends will typically contain about 0.1 weight percent to about 9.9 weight percent of poly(ε-caprolactone-co-p-dioxanone) copolymer, and most preferably about 0.5 weight percent to about 9.5 weight percent of poly(ε-caprolactone-co-p-dioxanone) copolymer. The major phase of the blend will comprise a poly(lactide) homopolymer and/or poly(lactide-co-glycolide) copolymer of about 99.9 weight percent to about 90.1 weight percent, and more preferably about 99.5 weight percent to about 90.5 weight percent.

The tertiary polymer blends of the present invention will contain sufficient amounts of poly(ε-caprolactone) and poly (p-dioxanone) homopolymers to effectively impart shapeability and palpability to the blend while retaining the strength, stiffness and BSR properties of the poly(lactide) homopolymer and/or poly(lactide-co-glycolide) copolymers. Furthermore, since it is known in the art that homopolymers more readily crystallize than copolymers, the addition of poly(ε-caprolactone) and poly(p-dioxanone) homopolymers has the additional ability to impart dimensional stability to the blends in comparison to those blends with poly(ε-caprolactone-co-p-dioxanone) copolymers.

The tertiary polymer blends will contain a combination of about 0.1 weight percent to about 9.9 weight percent of various amounts of poly(p-dioxanone) and poly(ε-caprolactone) homopolymers, and preferably about 0.5 weight percent to about 9.5 weight percent. The relative proportion of caprolactone) homopolymer to poly(p-dioxanone) homopolymer in the blend will typically contain about 5 weight percent to about 95 weight percent poly(ε-caprolactone), and preferably about 50 weight percent to about 95 weight percent poly(ε-caprolactone) homopolymer. The major phase of the blend will comprise a poly (lactide) homopolymer and/or poly(lactide-co-glycolide) copolymers of about 99.9 weight percent to about 90.1 weight percent, and more preferably about 99.5 weight percent to about 90.5 weight percent.

It is well within the abilities of one skilled in the art to choose whether to use a poly(lactide) homopolymer, a poly(lactide-co-glycolide) copolymer, or a combination thereof in the blends of the present invention. The skilled practitioner will base his choice, inter alia, on the physical properties required of the blend, e.g., BSR.

Articles such as medical devices are molded from the polymer blends of the present invention by use of various conventional injection and extrusion molding equipment equipped with dry nitrogen atmospheric chamber(s) at temperatures ranging from about 160° C. to about 230° C., more preferably from about 170° C. to about 220° C., with residence times of about 1 to about 10 minutes, more preferably from about 2 to about 5 minutes.

The blends of this invention can be melt processed by numerous conventional methods and equivalents thereof to prepare a vast array of useful devices. These blends can be injection or compression molded to make implantable medical and surgical devices, especially wound closure devices. The preferred wound closure devices are surgical clips, staples, suture anchors, tacks, pins, plates and screws, and sutures.

Alternatively, the blends can be extruded to prepare fibers. The filaments thus produced may be fabricated into medical devices such as sutures or ligatures, attached to surgical needles, packaged, and sterilized by known techniques. The blends of the present invention may be spun as multifilament yarn and woven or knitted to form sponges or gauze, (or nonwoven sheets may be prepared) or used in conjunction with other molded compressive structures as prosthetic devices within the body of a human or animal where it is desirable that the structure have high tensile strength and desirable levels of compliance and/or ductility. Useful embodiments include medical devices such as tubes, including branched tubes, for artery, vein or intestinal repair, nerve splicing, tendon splicing, sheets for tying up and supporting damaged surface abrasions, particularly major abrasions, or areas where the skin and underlying tissues are damaged or surgically removed.

Additionally, the blends can be molded to form films which, when sterilized, are useful as adhesion prevention barriers. Another alternative processing technique for the blends of this invention includes solvent casting, particularly for those applications where a drug delivery matrix is desired.

In more detail, the surgical and medical uses of the filaments, films, and molded articles of the present invention include, but are not necessarily limited to:

Knitted medical devices, woven or non-woven, and molded medical devices including:
a. burn dressings
b. hernia patches
c. medicated dressings
d. fascial substitutes
e. gauze, fabric, sheet, felt or sponge for liver hemostasis
f. gauze bandages
g. arterial graft or substitutes
h. bandages for skin surfaces
i. burn dressings
j. orthopedic pins, clamps, screws, and plates
k. clips
l. staples
m. hooks, buttons, and snaps
n. bone substitutes
o. needles
p. intrauterine devices
q. draining or testing tubes or capillaries
r. surgical instruments
s. vascular implants or supports
t. vertebral discs
u. extracorporeal tubing for kidney and heart-lung machines
v. artificial skin
w. stents
x. suture anchors and others.

Figure 2:
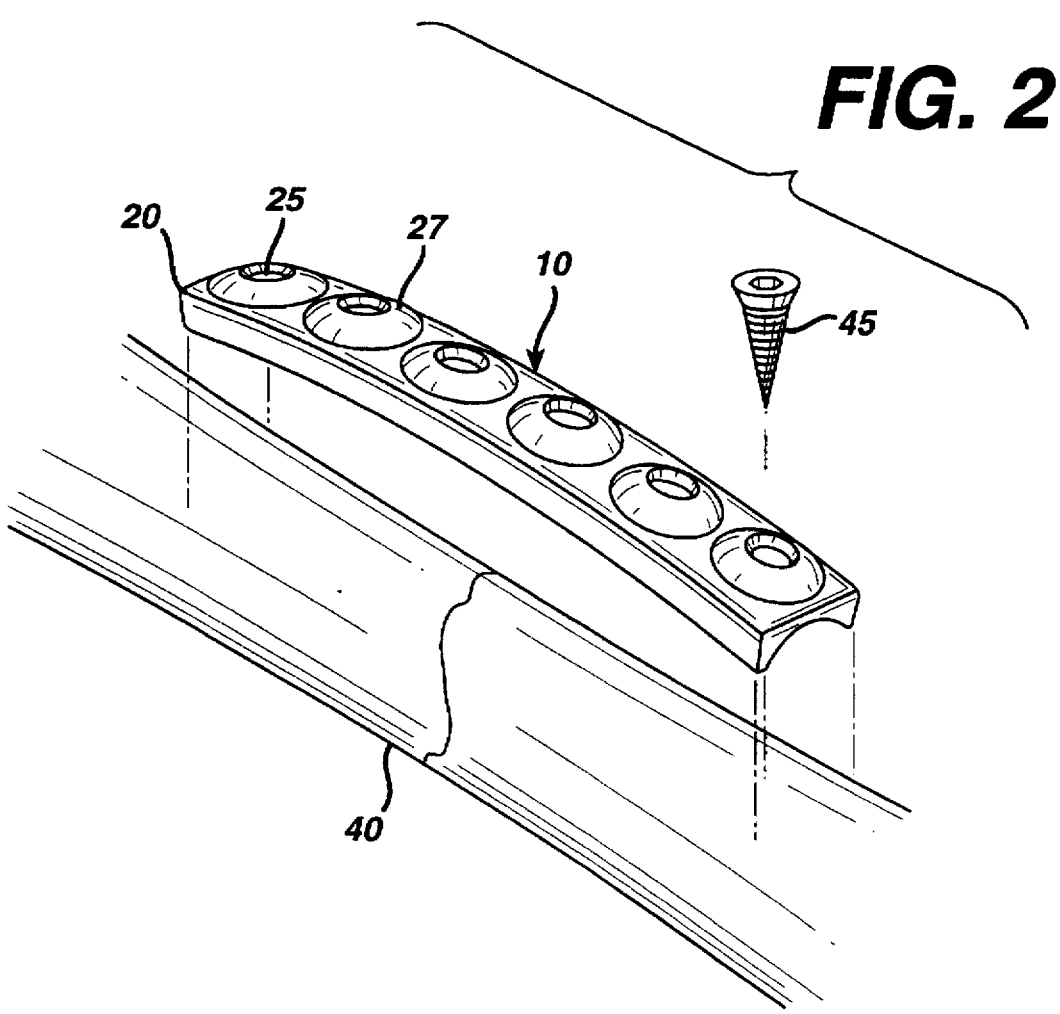
FIG. 2 is an illustration of a perspective view of a maxillofacial plate which can be manufactured from the polymer blends of the present invention.

Referring to FIG. 2, a specific medical device, a bone plate 10, is illustrated. Bone plate 10 can be manufactured from the polymer blends of the present invention. The bone plate 10 is seen to have frame 20 and a plurality of openings 25 therethrough for receiving fasteners such as bone screws 45. Raised shoulders 27 extend from frame 20 and surround each opening 25. The bone plate 10 may be heated to a temperature of from about 80° C. to about 120° C. in a conventional manner by, for example, immersing the bone plate in a heated water bath, radiant heating, convective heating, etc., and combinations thereof. When heated sufficiently, the plate 10 may be effectively shaped to conform to a body structure such as bone segment 40 by bending, twisting, etc., the frame 20. The plate 10 is then allowed to cool and the shaped plate 10 is then applied next to the body structure using conventional surgical techniques. As seen in FIG. 2, the plate 10 has been slightly bowed prior to being affixed to a bone section 40. Plate 10 may be molded from the polymer blends of the present invention using conventional molding apparatuses and conventional processes.

Figure 3:
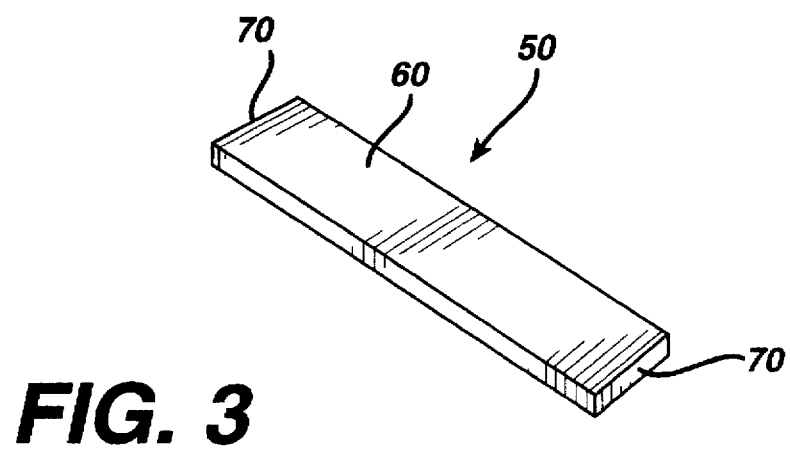
FIG. 3 is a perspective view of a test flex bar manufactured from a polymer blend of the present invention.
Figure 4:
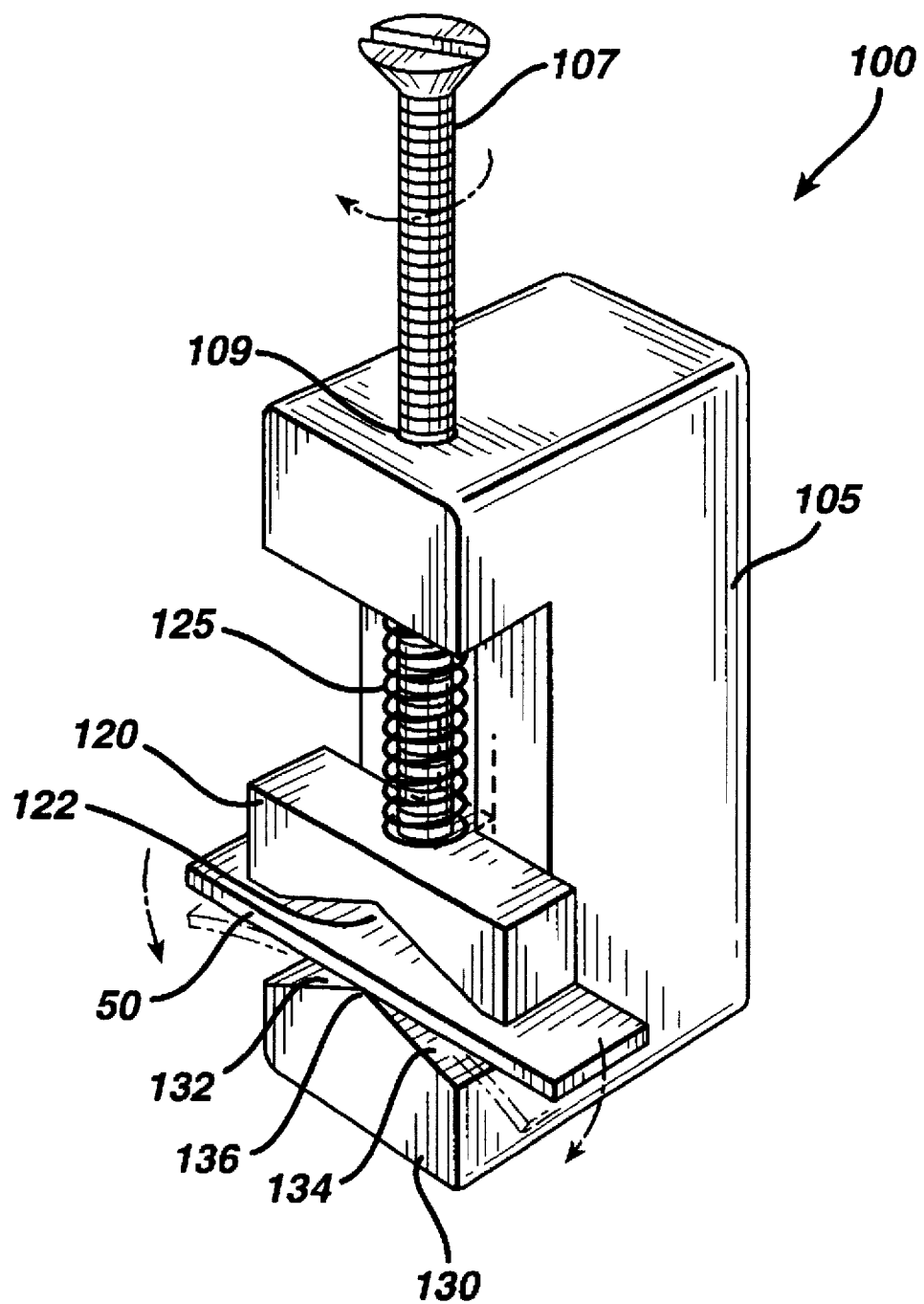
FIG. 4 is a perspective view of a test device used to test the bendability of the polymer blends of the present invention.

A test flex bar 50 manufactured from the polymer blends of the present invention is seen in FIG. 3. The rectangularly shaped flex bar 50 is seen to have elongated body section 60 having opposed ends 70. A testing device 100 for testing flex bars 50 is illustrated in FIG. 4. The device has a stationary frame 105 and a movable member 120 biased by helical spring member 125. Moveable member 120 is seen to be mounted to shaft member 107 which is free to slide through passage 109 in frame 105. A flex bar 50 fits into frame 105 resting upon base member 130 having sloping sides 132 and 134 which intersect at peak 136. The flex bar is contacted by movable member 120. When the flex bar 50 is heated, e.g., by hot water, the biased member 120 will cause flex bar 50 to bend about the peak 136 of base member 130. Moveable member 120 is seen to have cavity 122 corresponding to the configuration of basemember 130.

EXAMPLES

The following examples are illustrative of the principles and practice of this invention, although not limited thereto.

Numerous additional embodiments within the scope and spirit of the invention will become apparent to those skilled in the art. The examples describe new blends of aliphatic polyesters, potentially useful as biomedical devices.

In the synthetic process, the high molecular weight aliphatic polyesters are prepared by a method consisting of reacting lactone monomers via a ring opening polymerization at temperatures of 80° C. to 220° C., for 1 to 24 hours under an inert nitrogen atmosphere until the desired molecular weight and viscosity are achieved.

In the blending process, the polymer blends of the present invention are prepared by individually charging the synthesized aliphatic homo- and co-polyesters into a conventional mixing vessel. The homopolymers and copolymers are mixed at a temperature of 150° C. to 220° C., for 5 to 90 minutes until a uniformly dispersed polymer blend is obtained.

In the examples, high molecular weight aliphatic polyesters and blends thereof, are prepared and based upon lactone monomers such as glycolide, lactide, p-dioxanone, and ε-caprolactone.

In the examples which follow, the blends, polymers and monomers were characterized for chemical composition and purity (NMR, FT-IR), thermal analysis (DSC), melt theology (melt stability and viscosity), molecular weight (inherent viscosity), and baseline and in vitro mechanical properties (Instron stress/strain).

FT-IR was performed on a Nicolet FT-IR. Polymer samples were melt pressed into thin films. Monomers were pressed into KBr pellets. $^1$H NMR was performed on a 300 MHz NMR using $CDCl_3$ or HFAD as a reference.

Thermal analysis of blends, polymers and monomers was performed on a Dupont 912 Differential Scanning Calorimeter (DSC) at a heating rate of 10° C./min. A Fisher-Johns melting point apparatus was also utilized to determine melting points of monomers. Thermal gravimetric analysis was performed on a Dupont 951 TGA at a rate of 10° C./min. under a nitrogen atmosphere. Isothermal melt stability of the polymers was also determined by a Rheometrics Dynamic Analyzer RDA II for a period of 1 hour at temperatures ranging from 160° C. to 230° C. under a nitrogen atmosphere.

Inherent viscosities (I.V., dL/g) of the blends and polymers were measured using a 50 bore Cannon-Ubbolhode dilution viscometer immersed in a thermostatically controlled water bath at 25° C. utilizing chloroform or HFIP as the solvent at a concentration of 0.1 dL/g.

Melt viscosity was determined utilizing a Rheometrics Dynamic Analyzer RDA II at temperatures ranging from 16° C. to 230° C. at rate of 1° C./min. to 10° C./min. at frequencies of $1s^{-1}$ to $100s^{-1}$ under a nitrogen atmosphere.

Baseline and in vitro mechanical properties of cylindrical dumbbells of the blends were performed on an Instron model 1122 at a crosshead rate of 0.35 in/min. Specimen gauge length was 0.35 in., with a width of 0.06 in. Results are an average of 8 to 12 dumbbell specimens.

The cylindrical dumbbells were prepared by utilizing a CSI Mini-max injection molder equipped with a dry nitrogen atmospheric chamber at temperatures ranging from 170° C. to 220° C. with a residence time of 3 minutes.

In vitro studies were determined in a phosphate buffer solution (pH=7.27) at a temperature of 37° C. for periods of 1, 3, and 6 weeks. Cylindrical dumbbells (8 to 10 of a total weight of 2.4 to 3.0 grams) were placed in 100 ml of buffer solution.

Several synthetic and blending examples will be described in the following few pages. Parts and percentages where used are parts and percentages as specified as weight or moles.

Example 1

Synthesis of a 95:5 (tool/tool) poly(lactide-co-glycolide) copolymer

The method described below and utilized in this example is similar to those described in U.S. Pat. Nos. 4,643,191, 4,653,497, 5,007,923, 5,047,048 which are incorporated by reference, and is known to those skilled in the art.

To a flame dried 500 mL 1-neck round bottom flask equipped with an overhead mechanical stirrer and nitrogen inlet, 300 grams (2.08 moles) of L(−) lactide, 12.8 grams (0.110 moles) of glycolide, 0.53 grams ($7 \times 10^{-3}$ moles) of glycolic acid initiator, and 131 microliters of a 0.33M solution of stannous octcate catalyst were added.

The assembly was then placed in a high temperature oil bath at 185° C. The stirred monomers quickly began to melt. The low viscosity melt quickly increased in viscosity. Mechanical stirring of the high viscosity melt was continued for a total reaction time of 4 hours.

The 95:5 (mol/mol) poly(lactide-co-glycolide) copolymer was removed from the bath, cooled to room temperature under a stream of nitrogen, isolated and ground. The polymer was then dried under vacuum at 110° C. for 24 hours. Inherent viscosity using HFIP as a solvent was 1.95 dL/g.

Example 2

Synthesis of a 90:10 (mol/mol) poly(ε-caprolaptone-co-p-dioxanone) copolymer

The method described below in this example is similar to those described in U.S. Pat. Nos. 4,643,191, 4,653,497, 5,007,923, 5,047,048 which are incorporated by reference, and is known to those skilled in the art.

To a flame dried 500 mL 1-neck round bottom flask equipped with an overhead mechanical stirrer and nitrogen inlet, 251.13 grams (2.2 moles) of ε-caprolactone, 22.5 grams (0.22 moles) of p-dioxanone, 0.84 grams (0.011 moles) of glycolic acid initiator, and 147 microliters of a 0.33M solution of stannous octcate catalyst were added.

The assembly was then placed in a high temperature oil bath at 190° C. The stirred monomers quickly began to melt. The low viscosity melt quickly increased in viscosity. Mechanical stirring of the high viscosity melt was continued for a total reaction time of 24 hours.

The 90:10 (mol/mol) poly(ε-caprolactone-co-p-dioxanone) copolymer was removed from the bath, cooled to room temperature under a stream of nitrogen, isolated and ground. The polymer was then dried under vacuum at 40° C. for 24 hours. Inherent viscosity using HFIP as a solvent was 1.17 dL/g.

Example 3

Blending of a 95:5 (mol/mol) poly(lactide-co-glycolide) copolymer with a 90:10 (mol/mol) poly(ε-caprolactone-co-p-dioxanone) copolymer at a blended weight ratio of 95:5

29.45 grams of a 95:5 (mol/mol) poly(lactide-co-glycolide) prepared as described in Example 1 was melt blended with 1.55 grams of the 90:10 (mol/mol) poly(ε-caprolactone-co-p-dioxanone) copolymer of Example 2 at a weight ratio of 95:5 in a Brabender Plasti-corder mixer at a temperature of 170° C. for 23 minutes. The resulting blend

9 was removed from the Brabender mixer, cooled, ground and dried under vacuum at 50° C. for 24 hours. Inherent viscosity using HFIP as a solvent was 1.90 dL/g.

Example 4

Blending of a 95:5 (mol/mol) poly(lactide-co-glycolide) copolymer with a 90:10 (mol/mol) poly(ε-caprolactone-co-p-dioxanone) copolymer at a blended weight ratio of 99.5:0.5

30.845 grams of the 95:5 (mol/mol) poly(lactide-co-glycolide) copolymer is prepared in accordance with the procedure of Example 1 and is melt blended with 0.155 grams of a 90:10 (mol/mol) poly(ε-caprolactone-co-p-dioxanone) copolymer prepared in accordance with Example 2 at a weight ratio of 99.5:0.5 prepared in accordance with Example 3 in a Brabender Plasti-corder mixer at a temperature of 170° C. for 23 minutes. The blend is removed from the Brabender mixer, cooled, ground and dried under vacuum at 50° C. for 24 hours.

Example 5

Blending of a 95:5 (mol/mol) poly(lactide-co-glycolide) copolymer with a 90:10 poly(ε-caprolactone-co-p-dioxanone) copolymer at a blended weight ratio of 90.5:9.5

28.055 grams of a 95:5 (mol/mol) poly(lactide-co-glycolide) copolymer is prepared in accordance with the procedure of Example 1 and is melt blended with 2.945 grams of a 90:10 poly(ε-caprolactone-co-p-dioxanone) copolymer prepared in accordance with Example 2 at a weight ratio of 90.5:9.5 prepared in accordance with Example 3 in a Brabender Plasticorder mixer at a temperature of 170° C. for 23 minutes. The blend is removed from the Brabender mixer, cooled, ground and dried under vacuum at 50° C. for 24 hours.

Example 6

Blending of a 95:5 (mol/mol) poly(lactide-co-glycolide) copolymer with poly(ε-caprolactone) and poly(p-dioxanone) homopolymers at a blended weight ratio of 90.5:4.5:5.0

28.055 grams of a 95:5 (mol/mol) poly(lactide-co-glycolide) copolymer prepared as described in Example 1 was melt blended with 1.395 grams of poly(ε-caprolactone) and 1.55 grams of poly(p-dioxanone) homopolymers, as prepared and described in U.S. Pat. Nos. 4,643,191, 4,653,497, 5,007,923, 5,047,048 which are incorporated by reference, and are known to those skilled in the art, at a weight ratio of 90.5:4.5:5.0 in a Brabender Plasti-corder mixer at a temperature of 170° C. for 23 minutes. The blend was removed from the Brabender mixer, cooled, ground and dried under vacuum at 50° C. for 24 hours. Inherent viscosity using HFIP as a solvent was 1.84 dL/g.

Example 7

Blending of a 95:5 (mol/mol) poly(lactide-co-glycolide) copolymer with poly(ε-caprolactone) and poly(p-dioxanone) homopolymers at a blended weight ratio of 99.5:0.25:0.25

30.845 grams of a 95:5 (mol/mol) poly(lactide-co-glycolide) copolymer is prepared in accordance with the procedure of Example 1 and is melt blended with 0.775 grams each of poly(ε-caprolactone) and poly(p-dioxanone) homopolymers, prepared in accordance with the procedures disclosed in U.S. Pat. Nos. 4,643,191, 4,653,497, 5,007,923, 5,047,048 which are incorporated by reference, and are known to those skilled in the art, at a weight ratio of 99.5:0.25:0.25 prepared in accordance with Example 3 in a Brabender Plasticorder mixer at a temperature of 170° C. for 23 minutes. The blend is removed from the Brabender mixer, cooled, ground and dried under vacuum at 50° C. for 24 hours.

Example 8

Flex bar bending experiments on blends of poly(lactide-co-glycolide), poly(ε-caprolactone) and poly(p-dioxanone)

Flex bars 50 of the blends of Examples 3 and 6, 2 inches×0.375 inches×60 mils thick, used for shapeability testing (See FIG. 3), were prepared by compression molding utilizing a Carver Model 2696 Hydraulic Press at temperatures ranging from 150° C. to 220° C. for 10 minutes at pressures of 1,000 to 5,000 psi. Once formed, the flex bars 50 were slowly cooled to room temperature under pressure.

For bendability or shapeability testing, the flex bars 50 were placed in a bending testing device 100 as illustrated in FIG. 4. The bending device was then placed in a hot water bath (80°–100° C.), and the flex bar was bent to a 45° angle. Five flex bars 50 of each of the blends were then placed in vitro in a phosphate buffer solution (pH=7.27) at a temperature of 37° C. for periods of 1, 3, and 6 weeks. The change in the angle of the flex bars 50 from the horizontal was then measured. The results are shown in Table 1.

TABLE 1

BASELINE AND IN-VITRO SHAPEABILITY OF MELT BLENDS

| Blend Type | Wt. % | Composition | Baseline (0-day) Angle of bend (degrees) | In-Vitro Wk 1 Angle of bend (degrees) | % Loss | In-Vitro Wk 3 Angle of bend (degrees) | % Loss | In-Vitro Wk 6 Angle of bend (degrees) | % Loss |
|---|---|---|---|---|---|---|---|---|---|
| Binary Blends | 95/5 | (L/G 95/5) - (PCL/PDS 90/10) | 45 | 45 | 0 | 45 | 0 | 45 | 0 |
| Tertiary Blends | 95/5/5 | (L/G 95/5) - (PDS) - (PCL) | 45 | 45 | 0 | 45 | 0 | 45 | 0 |

Example 9

A patient having a fractured femur is prepared for surgery using conventional surgical techniques. The patient's femur is exposed using conventional surgical techniques so that the bone fracture site 40 is exposed as seen in FIG. 2. The surgeon takes a bone plate 10 manufactured from the polymer and copolymer blends of the present invention and immerses it in a vessel containing sufficiently warm water e.g., 80°–100° C. for a sufficient amount of time to effectively soften the plate 10. The plate 10 is removed from the vessel and the surgeon shapes the bone plate 10 by bending it and then allows it to cool for a sufficient amount of time so that it effectively retains its shape. The plate 10 is then mounted to fracture site 40 in a conventional manner using conventional biocompatible bone screws 45. The patient's thigh is then closed using conventional surgical techniques.

The polymer blends of the present invention have many advantages over the polymer blends of the prior art. For example, in the development of a maxillofacial fixation device one of the concerns involves the ability of the device to be shaped by the surgeon during surgery to the contours of, for example, a fractured bone 40 as seen in FIG. 2. Once contoured to the fractured bone, the device must retain its shape. That is, the polymer must have shape retention characteristics.

For example, as found for the binary blends of this invention, by the addition of small amounts of a poly(ε-caprolactone-co-p-dioxanone) copolymer to a poly(lactide-co-glycolide) copolymer, better shape retention can be obtained. That is, by heating the plate to 80°–120° C. to bend it to the shape of the fractured bone, the poly(ε-caprolactone-co-p-dioxanone) copolymer will melt, causing the plate to "flow" and bend more easily. Once the plate has cooled, the poly(ε-caprolactone-co-p-dioxanone) copolymer crystallizes, "locking" the newly contoured shape into the plate.

That is, when flex bars 50 of the present invention (FIG. 3) are bent at elevated temperatures (80°–12° C.) by a mechanical assist device 100 (FIG. 4) to a 45 degree angle, then held at this position until cooled to room or body temperature, virtually no change in angular shape of the flex bar occurs over 6 weeks in vitro at 37° C. (buffer solution, pH=7.27) (See Table 2).

semi-crystalline polymers are added. For example, as shown in Table 2 and FIG. 1, virtually no difference is observed in the BSR profiles of a 95:5 (mol/mol) poly(lactide-co-glycolide) copolymer, and a blend of a 95:5 (mol/mol) poly(lactide-co-glycolide) copolymer and a 90:10 poly(ε-caprolactone-co-p-dioxanone) copolymer at a blend ratio of 95/5 weight percent.

These results are a strong indication that small additions of these semi-crystalline polymers to poly(lactide) homopolymers and/or poly(lactide-co-glycolide) copolymers does not limit their physical properties.

Additionally, these blends will have improved palpability. Since poly(ε-caprolactone-co-p-dioxanone) copolymers can surface erode, the device will slowly dissolve away rather than fragmenting into small granules. Formation of small granules of polymer can lead to tissue reaction.

Therefore, binary blends consisting of a poly(lactide) homopolymers and/or poly(lactide-co-glycolide) copolymers with poly(ε-caprolactone-co-p-dioxanone) copolymers will give desirable properties such as shape retention and palpability while maintaining the high strength, stiffness and BSR of the poly(lactide) homopolymers and/or poly(lactide-co-glycolide) copolymers.

Furthermore, tertiary blends of poly(lactide) homopolymers and/or poly(lactide-co-glycolide) copolymers with poly(ε-caprolactone) and poly(p-dioxanone) homopolymers will also impart the desirable properties of shape retention and palpability while maintaining the high strength, stiffness and BSR of the poly(lactide) homopolymers and/or poly

TABLE 2

BASELINE AND IN-VITRO BSR TENSILE STRENGTH OF MELT BLENDS

| Blend Type | Wt. % | Composition | Baseline (0-day) Yield Strength psi | In-Vitro BSR Wk 1 Yield Strength psi | % Loss | In-Vitro BSR Wk 3 Yield Strength psi | % Loss | In-Vitro BSR Wk 6 Yield Strength psi | % Loss |
|---|---|---|---|---|---|---|---|---|---|
| Binary Blends | 95/5 | (L/G 95/5) - (PCL/PDS 90/10) | 9800 | 8200 | 16 | 6600 | 32 | 4900 | 50 |
| Tertiary Blends | 95/5/5 | (L/G 95/5) - (PDS) - (PCL) | 7900 | 5500 | 31 | 4800 | 39 | 3200 | 60 |

This data strongly indicates that shapeability in a device can be obtained by utilizing small amounts of semi-crystalline, poly(ε-caprolactone-co-p-dioxanone) copolymers or poly(ε-caprolactone) and poly(p-dioxanone) homopolymers a blend with poly(lactide) homopolymers and/or poly(lactide-co-glycolide) copolymers.

These results are in direct contrast to the previous art which describes that the addition of a large amount of a ductile polymer to poly(lactide) homopolymers and/or poly (lactide-co-glycolide) copolymers is necessary to allow the device to be bent to the contours of the fractured bone. That is, the bendability or shapeability occurs through a lowering of the stiffness of the blend. This allows the surgeon to bend the device, causing crazes to form, resulting in permanent deformation of the device.

However, due to the addition of a large amount of ductile polymer to these blends, the blends of the previous art can lose a great deal of strength, stiffness and BSR. Since high strength, stiffness and a long BSR profile are required for correct fracture fixation, the loss of such properties is detrimental to the development of devices for plastic and reconstructive, and orthopedic surgical applications.

Lower strength, stiffness and BSR will not occur for the blends of the present invention, since only small amounts of (lactide-co-glycolide) copolymers. In addition, since it is well known that homopolymers more readily crystallize than copolymers, the tertiary blends will have improved dimensional stability in comparison to the binary blends.

Medical devices made from the polymer blends of the present invention are typically pre-packaged by the manufacturer using conventional packages and packaging materials. The devices in the packages are then typically sterilized by the manufacturer using conventional sterilization processes and procedures, including ethylene oxide, radiation, heat, etc. Although not desirable, the medical devices of the present invention can be sterilized at the point of use, e.g., the hospital, but only if the devices have not been previously sterilized.

Although this invention has been shown and described with respect to detailed embodiments thereof, it will be understood by those skilled in the art that various changes in form and detail thereof may be made without departing from the spirit and scope of the claimed invention.

We claim:

1. A method of conforming the shape of a bioabsorbable medical device to a body structure comprising the steps of:

heating a bioabsorbable medical device sufficiently to effectively allow the medical device to be formed;

conforming the heated medical device to a shape of a body structure;

cooling the medical device sufficiently so that the device effectively retains the shape, wherein the medical device comprises a bioabsorbable polymer blend which comprises:

a major phase comprising about 90.1 weight percent to about 99.9 weight percent of a polymer selected from the group consisting of poly(lactide) homopolymers and poly(lactide-co-glycolide) copolymers, and combinations thereof; and, a minor phase comprising about 0.1 weight percent to about 9.9 weight percent of a mixture of poly(ε-caprolactone) and poly(p-dioxanone) homopolymers, wherein said blend has a weight fraction of the major phase and minor phase equal to 100.0 weight percent.

2. A method of conforming the shape of a bioabsorbable medical device to a body structure comprising the steps of:

heating a bioabsorbable medical device sufficiently to effectively allow the medical device to be formed;

conforming the heated medical device to a shape of a body structure;

cooling the medical device sufficiently so that the device effectively retains the shape, wherein the medical device comprises a bioabsorbable polymer blend which comprises:

a major phase comprising about 90.1 weight percent to about 99.9 weight percent of a polymer selected from the group consisting of poly(lactide) homopolymers and poly(lactide-co-glycolide) copolymers, and combinations thereof; and, a minor phase comprising about 0.1 weight percent to about 9.9 weight percent of a copolymer of poly(ε-caprolactone-co-p-dioxanone), wherein said blend has a weight fraction of the major phase and minor phase equal to 100.0 weight percent.

\* \* \* \* \*